(12) United States Patent
Jensen et al.

(10) Patent No.: US 12,721,504 B2
(45) Date of Patent: Sep. 1, 2026

(54) ENDOSCOPE WITH A BENDING SECTION HAVING A CUT-OUT FOR A WORKING CHANNEL

(71) Applicant: AMBU A/S, Ballerup (DK)

(72) Inventors: Thomas Bachgaard Jensen, Copenhagen (DK); Kaspar Matthison-Hansen, Helsignør (DK)

(73) Assignee: AMBU A/S, Ballerup (DK)

( * ) Notice: Subject to any disclaimer, the term of this patent is extended or adjusted under 35 U.S.C. 154(b) by 546 days.

(21) Appl. No.: 18/037,609

(22) PCT Filed: Nov. 16, 2021

(86) PCT No.: PCT/EP2021/081865

§ 371 (c)(1),
(2) Date: May 18, 2023

(87) PCT Pub. No.: WO2022/106421

PCT Pub. Date: May 27, 2022

(65) Prior Publication Data

US 2023/0414080 A1 Dec. 28, 2023

(30) Foreign Application Priority Data

Nov. 23, 2020 (DE) ..................... 10 2020 130 951.1

(51) Int. Cl.
*A61B 1/005* (2006.01)
*A61B 1/018* (2006.01)

(52) U.S. Cl.
CPC .......... *A61B 1/0055* (2013.01); *A61B 1/0057* (2013.01); *A61B 1/018* (2013.01)

(58) Field of Classification Search
CPC .... A61B 25/0054; A61B 1/0057; A61B 1/018
See application file for complete search history.

(56) References Cited

U.S. PATENT DOCUMENTS 4,651,718 A 3/1987 Collins et al.
5,329,935 A 7/1994 Takahashi
(Continued)

FOREIGN PATENT DOCUMENTS

DE 102014107430 A1 12/2014
EP 0301288 A1 2/1989
(Continued)

OTHER PUBLICATIONS

Search report, and English translation thereof, in German Application No. 10 2020 130 951.1, issued Aug. 26, 2021.
(Continued)

*Primary Examiner* — Anh Tuan T Nguyen
*Assistant Examiner* — Rynae E Boler
(74) *Attorney, Agent, or Firm* — Faegre Drinker Biddle & Reath LLP

(57) ABSTRACT

A endoscope including a handle, a shaft and a distal tip unit. The shaft includes a bending section, a working channel and a steering wire for controlling a bending movement of the bending section. The bending section includes segments, flexible hinge members provided between adjacent segments, an inner lumen adapted for accommodating the working channel, and steering wire lumens adapted for accommodating the steering wire. The working channel is gradually/continuously/linearly guided away from a position close to a centerline of the endoscope shaft in the bending section.

8 Claims, 3 Drawing Sheets

(56) References Cited

U.S. PATENT DOCUMENTS

| | | | | |
|---|---|---|---|---|
| 7,320,700 | B2 | 1/2008 | Cooper et al. | |
| 10,149,605 | B2 | 12/2018 | Petersen et al. | |
| 10,321,804 | B2 | 6/2019 | Jacobsen et al. | |
| 10,624,531 | B2 | 4/2020 | Matthison-Hansen | |
| 10,646,107 | B2 | 5/2020 | Matthison-Hansen et al. | |
| 11,337,588 | B2 | 5/2022 | Matthison-Hansen et al. | |
| 11,471,031 | B2 | 10/2022 | Jensen | |
| 11,622,674 | B2 | 4/2023 | Jensen | |
| 2003/0083550 | A1 | 5/2003 | Miyagi | |
| 2005/0131279 | A1* | 6/2005 | Boulais | A61B 1/0016 600/141 |
| 2007/0208224 | A1* | 9/2007 | Olson | A61M 25/007 600/141 |
| 2007/0233040 | A1* | 10/2007 | Macnamara | A61B 1/0055 604/523 |
| 2011/0306831 | A1 | 12/2011 | Køhnke et al. | |
| 2012/0238952 | A1* | 9/2012 | Mitchell | A61M 25/0147 604/95.04 |
| 2015/0230692 | A1 | 8/2015 | Matsuda et al. | |
| 2017/0245738 | A1 | 8/2017 | Fujitani et al. | |
| 2020/0000312 | A1 | 1/2020 | Nakaji | |
| 2020/0107892 | A1 | 4/2020 | Cooper et al. | |
| 2022/0061645 | A1 | 3/2022 | Jochumsen et al. | |

FOREIGN PATENT DOCUMENTS

| | | | |
|---|---|---|---|
| EP | 1551277 | B1 | 8/2007 |
| EP | 2155037 | B1 | 4/2017 |
| EP | 3207853 | A1 | 8/2017 |
| JP | H0663005 | A | 3/1994 |
| JP | H1033467 | A | 2/1998 |

OTHER PUBLICATIONS

International Search Report and Written Opinion in International Application No. PCT/EP2021/081865, dated Feb. 9, 2022, 10 pages.

* cited by examiner

ENDOSCOPE WITH A BENDING SECTION HAVING A CUT-OUT FOR A WORKING CHANNEL

CROSS REFERENCE TO RELATED APPLICATIONS

This application is a National Phase entry under 35 U.S.C. § 371 of International Application No. PCT/EP2021/081865, filed Nov. 16, 2021, which claims the benefit of and priority from German Patent Application No. DE 10 2020 130 951.1, filed Nov. 23, 2020; said applications are incorporated by reference herein in their entirety.

The present disclosure relates to an endoscope comprising: a distal tip unit configured to be inserted into a patient's body cavity; a proximal endoscope handle comprising an operating unit/handle wheel for steering the distal tip unit; an endoscope shaft/insertion tube connecting the endoscope handle and the distal tip unit and comprising a bending section; a working channel provided in the endoscope shaft and extending from the endoscope handle towards the distal tip unit; and a steering wire for controlling a bending movement of the bending section, the steering wire being connected to the operating unit and extending through the endoscope shaft. The bending section comprises: a proximal end segment; a plurality of intermediate segments; a distal end segment connected to the distal tip unit; flexible hinge members provided between adjacent segments of the proximal end segment, the plurality of intermediate segments and the distal end segment; an inner lumen adopted for accommodating the working channel; and (dedicated) steering wire lumens adapted for accommodating the steering wire (in an assembled state of the endoscope).

PRIOR ART

Endoscopes and similar specialized instruments such as bronchoscopes, arthroscopes, colonoscopes, laparoscopes, gastroscopes and duodenoscopes are well known from the state of the art and are used for visual examination and diagnosis of hollow organs and body cavities, as well as to assist in surgery, e.g. for a targeted tissue sampling. Basically, a distal tip unit of an endoscope, which is connected to an endoscope handle via an endoscope shaft, can be inserted into a hollow organ or body cavity to be investigated with the endoscope. Both reusable and disposable endoscopes are known from the state of the art.

Known endoscopes usually contain (a) steering/control wire(s) that is/are pulled and released to bend a (flexible) bending section of the endoscope, such as a flexible shaft, in order to tilt the distal tip unit. The rotating force being applied to (a) handle wheel(s) provided at the endoscope handle by a user is basically transmitted into a pulling force acting on the steering wire in an axial direction of the steering wire. Thereby, the connection of the steering wire to the handle wheel is essential for transmitting the rotating force from the handle wheel to the steering wire.

In addition, for guiding medical instruments, such as forceps, into the patient's body cavity, a working channel is arranged or formed within the endoscope shaft. In known endoscopes, this working channel is usually implemented/formed as a flexible tube arranged/accommodated/supported in a lumen extending through the endoscope shaft in a longitudinal direction from the endoscope handle to the distal tip unit. Such a conventional endoscope is disclosed for example in U.S. Pat. No. 10,321,804 B2. In particular, U.S. Pat. No. 10,321,804 B2 discloses a bending section of an endoscope molded in a single piece of polymer material. The bending section comprises a number of bending segments kept/held together by bendable hinges. Steering wires are threaded through holes in the wall of the bending segments. The holes are usually already formed in the molding process. Further, the bending section comprises one lumen for a working channel and one lumen for electrical wires.

As endoscopes are usually used for visual examination and diagnosis of hollow organs and body cavities, an optical system for imaging, such as a camera unit, and illuminating/lighting means for illuminating the body cavity, for example light-emitting diodes or an end portion of a light fibre bundle, are arranged at the distal tip unit of a conventional endoscope. Due to the optical system and the illuminating means being arranged at the distal tip unit, the space provided for the working channel at the distal tip unit is limited.

Therefore, in order to provide sufficient space for the optical system and for the illuminating means, it is for example known from another document DE 10 2014 107 430 A1 that the working channel of an endoscope may be guided from a central position near the centerline of the endoscope shaft to a position at the outer circumference of the endoscope shaft via a guide element in the form of a ramp provided in a transition zone between the bending section and the distal tip unit.

However, providing additional guide elements increases the number of components and thus complicates an assembly of the endoscope. Moreover, providing a rather abrupt transition/displacement from a central position near the centerline of the endoscope shaft to a position close to the outer circumference of the endoscope shaft (which is the case when the transition zone is only provided in a small area of the endoscope shaft like in an area between the bending section and the distal tip unit) may be disadvantageous with respect to the guidance of the medical instrument through the working channel (due to potential kinking/buckling of the working channel). In particular, there may be high friction forces on medical instruments/tools guided through the working channel.

BRIEF DESCRIPTION OF THE DISCLOSURE

The tasks and objectives of the present disclosure are to eliminate or at least to reduce the disadvantages of the prior art. In particular, an endoscope having a bending section as part of an endoscope shaft shall be provided, in which sufficient space is available in a distal tip unit arranged on a distal end side of the bending section for a working channel, for an optical system such as a camera unit and for illuminating means. Further, the functional integrity and stability of the working channel shall not be endangered due to severe kinking/buckling of the working channel. In addition, no separate guide elements such as a ramp shall be provided.

The tasks and objectives are solved by an endoscope in accordance with claim 1. Advantageous embodiments are claimed in the dependent claims and/or are explained below.

In the present disclosure, "distal" basically means "in a direction away from a user/physician towards a patient" and "proximal" basically means "in a direction towards the user/physician away from the patient".

The present disclosure relates to an endoscope, in particular single-use endoscope, comprising: a distal tip unit configured to be inserted into a patient's body cavity; a proximal endoscope handle comprising an operating unit (handle wheel) for steering the distal tip unit; an endoscope shaft (insertion tube) connecting the endoscope handle and the distal tip unit and comprising a bending section; a working channel provided in the endoscope shaft and extending from the endoscope handle towards the distal tip unit; and a steering wire (preferably a steel wire) for controlling a bending movement of the bending section. The steering wire is connected to the operating unit and extends through the endoscope shaft. The bending section comprises: a proximal end segment; a plurality of intermediate segments; a distal end segment connected to the distal tip unit; flexible hinge members provided between adjacent segments of the proximal end segment, the plurality of intermediate segments and the distal end segment; an inner lumen adopted for accommodating the working channel; and (dedicated) steering wire lumens adapted for accommodating the steering wire (in an assembled state of the endoscope). The core idea of the present disclosure is that the working channel is gradually/continuously/linearly guided away from a position close to a centerline of the endoscope shaft in the bending section. The inner lumen/central passage of the bending section has a radially outwardly extending cut-out portion (having basically a rounded shape) for accommodating/supporting the working channel and a depth of the cut-out portion (gradually) increases along the bending section from the proximal end segment to the distal end segment.

The centerline may be defined as an axially extending middle axis, i.e. a middle axis extending in the proximal-distal-direction of the endoscope shaft.

The working channel may be arranged closer to the centerline of the endoscope shaft in the proximal end segment of the bending section compared to the distal end segment of the bending section. In other words, the working channel may be arranged closer to an outer circumference of the endoscope shaft in the distal end segment of the bending section compared to the proximal end segment of the bending section.

Preferably, the working channel gradually transitions from a position close to the centerline of the endoscope shaft in the proximal end segment of the bending section to a position close to the outer circumference of the endoscope shaft in the distal end segment of the bending section. Said differently, the working channel may be gradually guided away from a centerline of the endoscope shaft/may transition to a position closer to an outer circumference of the endoscope shaft from a proximal end side of the bending section towards a distal end side of the bending section.

In other words, the working channel is guided from a position substantially concentric with respect to the endoscope shaft to a position eccentric with respect to the endoscope shaft in the bending section. I.e. at the concentric position the center point of the working channel is arranged on or in close vicinity to the centerline of the endoscope shaft, whereas at the eccentric position the center point is distanced from the centerline. Thereby, the transition between the concentric position to the eccentric position is gradual/continuous/linear.

In particular, an entire length of the bending section is used for the smooth displacement of the working channel from a center position (a position close to the centerline of the endoscope shaft) towards a position closer to the side wall/outer circumference (i.e. an outer circumferential position). The endoscope is thus preferably configured/adapted so that the working channel is continuously/gradually moved/guided away from the center position to the outer circumferential position at least along the entire bending section of the endoscope shaft.

The smooth displacement of the working channel from the center/central position to the outer circumferential position prevents kinking of the working channel and reduces friction forces on surgical instruments/tools compared to an abrupt displacement. According to the present disclosure, no additional guide elements are necessary for guiding the working channel towards the outer circumferential position. Moreover, the endoscope according to the present disclosure provides sufficient space in the distal tip unit for the working channel, an optical system and illuminating means.

The inner lumen of the bending section is preferably a central passage through the segments (the proximal end segment, the plurality of intermediate segments and the distal end segment) of the bending section and is adapted/has a cross-sectional shape to accommodate the working channel/a bendable tube providing the working channel. The central passage thus preferably extends in an axial direction of the endoscope shaft between the endoscope handle and the distal tip unit.

In particular, the inner lumen of the bending section is one large lumen for the working channel and for additional tubes, sleeves or wires.

According to a preferred embodiment, the central passage can thus be configured to accommodate/support further tubes/sleeves/wires, in particular a waterjet tube, a rinsing tube, an insufflation tube, a wire tube/sleeve, electrical wires, etc. so that the distal tip unit, in particular the camera system and/or the illuminating means of the distal tip unit, can be rinsed, purified, supplied with electrical power, etc.

The inner lumen/central passage preferably has a non-circular cross sectional shape. In other words, a radial extension of the inner lumen is preferably smaller in a circumferential area of the bending section where the steering wire lumen(s) is/are provided compared to a circumferential area of the bending section where the steering wire lumen(s) is/are not provided, seen in a cross-sectional view. Once again differently said, the inner lumen preferably extends into a bending section material (in a circumferential area) between two steering wire lumens.

Particularly preferred, the inner lumen forms a four-leaf clover, seen in a cross sectional view.

According to the present disclosure, it may thus be expedient when the cross-sectional shape of the central passage is formed as a four-leaf clover, so that an inner single lumen defined by the central passage extends into the bending section material (in a circumferential area) between the dedicated steering wire lumens. With this configuration, the space defined by the central passage can be used to the maximum.

The bending section is preferably made from a polymer/plastic material. Especially preferred the bending section is made from a thermoplastic polymer, e.g. polystyrene (PS), polycarbonate (PC), acrylonitrile butadiene styrene (ABS), polyoxymethylene (POM), etc. However also other (thermoplastic) polymers are basically conceivable.

In particular, the bending section is formed/molded as a one-piece/single piece/integral part of a polymer material. This means, that it is preferable when the proximal end segment, the plurality of intermediate segments, the distal end segment and the hinge members are formed in one piece/one part/integrally/as a single component/part. The bending section is especially preferred an (injection) molded part/is manufactured using an injection-molding process. However, the bending section may be manufactured by an alternative manufacturing method, such as 3D printing.

Thus, an assembly of the endoscope can be facilitated to a great extent due to the reduction of the number of components.

Preferably, the bending section is configured for two-plane bending/is configured to bend in at least four directions, in particular in an up-direction, in a down-direction, in a right-direction and in a left-direction. However, also one-plane bending is conceivable.

The steering wire lumens may be axially extending passages, i.e. passages extending in an axial direction of the endoscope shaft. These axially extending passages may be formed in an outer circumferential area of the endoscope shaft/of the bending section. Especially preferred the steering wire lumens may be equally angularly spaced. For example, a plurality of steering wire lumens, in particular four steering wire lumens, may be provided.

According to a preferred embodiment, the bending section may comprise four steering wire lumens and two steering wires may be provided. In other words, the bending section may be controlled by two steering wires arranged in four steering wire lumens. Each steering wire of the two steering wires may be accommodated in two steering wire lumens in the assembled state of the endoscope, and a middle section of each steering wire may be fixed/fixated/ locked at a distal end of the bending section, e.g. by forming a loop. It is however also conceivable that a separate steering wire is provided in each steering wire lumen. This means that also four steering wires may be provided.

Further, it may be advantageous, if adjacent segments (of the proximal end segment, the plurality of intermediate segments and the distal end segment) are connected by two, preferably diametrically opposed arranged, hinge members. Hence, adjacent segments are able to bend/pivot, while being safely connected.

According to a further preferred embodiment, the hinge members between adjacent segments may be shifted by 90° relative to the hinge members connecting each of said adjacent segments to the corresponding previous or following adjacent segment. I.e. when considering the circular segments as a clock, a first segment and a second segment are connected with hinge members arranged at 12 and 6, whereas the hinge members connecting the second segment and a third segment are arranged at 3 and 9 and so on. In other words, the hinge members connecting two adjacent segments representing a pair of segments can be arranged diametrically opposed and shifted by 90° compared to adjacent pairs of segments. Thus, the manoeuvrability of the endoscope is enhanced, two-plane bending is enabled, while simultaneously the structural integrity of the bending section is ensured.

Preferably, the cut-out portion may be formed between two of the circumferentially distributed steering wire lumens. The cut-out portion represents an effective way for supporting and guiding the working channel without the need for additional components, thus facilitating the assembly of the endoscope.

Said differently, the inner lumen may have a cut-out portion for accommodating the working channel, the cut-out portion may be provided in an circumferential area between two steering wire lumens of the plurality of steering wire lumens, the cut-out portion may have a depth (with respect to a central axis of the endoscope shaft) by which the cut-out portion extends into a bending section material, wherein the depth of the cut-out portion increases (from the proximal end segment via the plurality of intermediate segments) towards the distal end segment of the bending section.

Particularly preferred, the depth of the cut-out portion into the bending section material may be greater in the distal end segment than in an adjacent first intermediate segment, and the depth of the cut-out portion into the bending section material may be greater in the first intermediate segment than in an adjacent second intermediate segment, and so on.

In other words, the individual segments of the bending section comprising the proximal end segment, the plurality of intermediate segments and the distal end segment may basically/essentially be annular/ring-shaped and a thickness (in a radial direction) of the ring-shaped/annular individual segments may (gradually) decrease towards the distal end segment of the bending section (in the circumferential area) where the cut-out portion for the working channel is provided.

This means that the thickness (in the radial direction) of the distal end segment in the circumferential area where the cut-out portion is provided may be smaller than the thickness of an adjacent first intermediate segment in the circumferential area where the cut-out portion is provided, and the thickness of the first intermediate segment in the circumferential area where the cut-out portion is provided may be smaller than the thickness of an adjacent second intermediate segment in the circumferential area where the cut-out portion is provided, and so on.

One could thus also say that the central passage preferably has a cut-out with a given depth into the material of the individual segments (in the circumferential area) between two steering wire lumens, wherein the cut-out starts at a first cut-out segment (e.g. the proximal end segment), and the depth of the cut-out into the material increases towards a distal end of the bending section, and the cut-out continues through the distal end segment.

Once again differently said, one of the (circumferential) areas between two dedicated steering wire lumens may be provided with a further/deeper cut-out into the material forming the bending section, wherein the cut-out provides a space for the working channel, wherein the cut-out extends in a longitudinal direction with a cut-out depth gradually increasing towards a distal end of the bending section (towards the distal end segment).

The cut-out/the cut-out portion is preferably formed/ constituted by one cloverleaf of the four-leaf-clover shaped inner lumen of the bending section.

To sum up, the inner lumen of the bending section may form a four-leaf clover with the inner lumen being extended into the bending section material between dedicated steering wire lumens. One of the areas between two dedicated steering wire lumens may be provided with a further/deeper cut-out into the material forming the bending section. This further cut-out may provide space for a working channel. The cut-out preferably extends in a longitudinal/axial direction of the bending section with a cut-out depth gradually increasing towards the distal tip unit, i.e. in distal direction. The inner lumen of the bending section is preferably one large lumen for tubes, wires and the working channel extending between the endoscope handle and the distal tip unit. Further to this, each steering wire may have at least one lumen in the bending section material for guiding the steering wire. The purpose of the gradually increasing cut-out depth for the working channel in the bending section is to gradually move the working channel closer to the outer circumference of the bending section in order to place the working channel opening in the distal tip unit close to the outer circumference. So the working channel is preferably gradually moved away from a centerline of the insertion tube/endoscope shaft and closer to the outer circumference in the bending section.

Expressed in still other words, the disclosure relates to an endoscope, a bending section of which comprises a number of segments including a proximal end segment, a distal end segment and a number of intermediate segments. The bending section further comprises hinge members provided between adjacent segments, wherein the segments and the hinge members are formed in a single-piece of a polymer material. Further, the bending section comprises dedicated steering wire lumens adapted for accommodating steering wires for controlling movement of the bending section and a central passage extending through the segments and adapted in cross-sectional shape to accommodate a bendable tube providing the working channel. The central passage extends into the bending section material between dedicated steering wire lumens. Further, the central passage has a cut-out with a given depth into the material of the segments (in a circumferential area) between two steering wire lumens. The cut-out starts at a first cut-out segment (e.g. the proximal end segment), the depth of the cut-out into the material increases towards the distal end segment of the bending section and the cut-out continues through the distal end segment.

BRIEF DESCRIPTION OF FIGURES

The disclosure is explained in more detail below using preferred embodiments and referring to the accompanying figures.

The figures are schematic in nature and serve only to understand the disclosure. Identical elements are marked with the same reference signs.

DETAILED DESCRIPTION OF A PREFERRED EMBODIMENT

Figure 1:
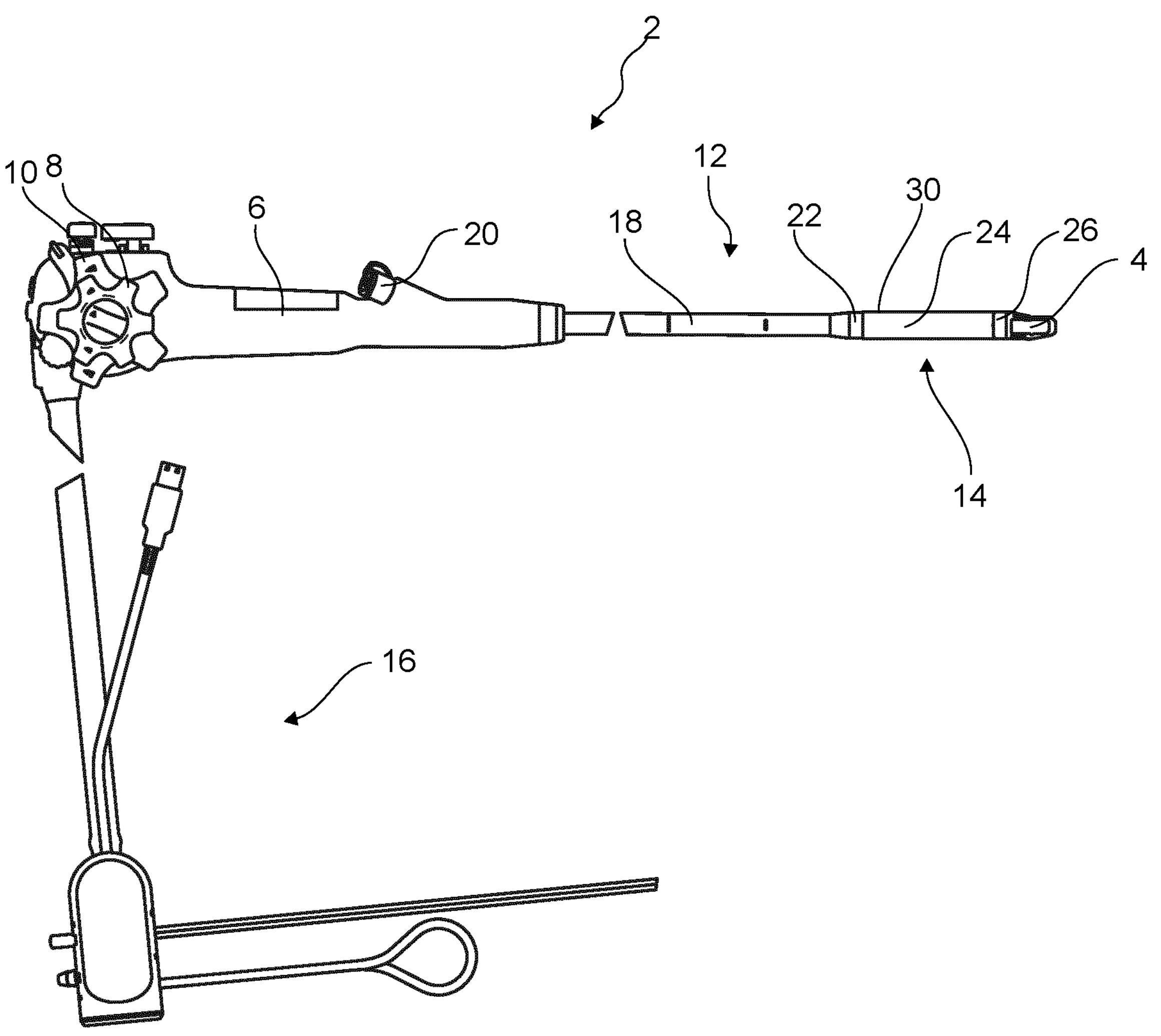
FIG. 1 is a plan view showing an endoscope according to the present disclosure.

In FIG. 1, an endoscope 2 is shown. The endoscope 2 is preferably a single-use endoscope. The endoscope 2 comprises a distal tip unit 4, which is configured to be inserted into a patient's body cavity. Further, the endoscope 2 comprises a proximal endoscope handle (handle unit) 6 designed to be held by a user/physician and being configured as a housing for accommodating operating parts (not shown) of the endoscope 2. The endoscope handle 6 comprises two handle wheels (operating units), namely a first handle wheel 8 and a second handle wheel 10, for steering the distal tip unit 4. In particular, the first handle wheel 8 and the second handle wheel 10 can both be rotated/turned by the user. The first handle wheel 8 and the second handle wheel 10 are arranged coaxially, i.e. can be rotated around a common rotational axis. The endoscope 2 further comprises an endoscope shaft (insertion tube) 12 extending from the endoscope handle 6 to the distal tip unit 4 and thus connecting the endoscope handle 6 and the distal tip unit 4. The endoscope shaft 12 comprises a bending section 14 at an end portion thereof. Moreover, a connector unit 16 for connecting the endoscope 2 to a supply unit is shown in FIG. 1.

The endoscope 2 has an internal working channel 18, which is formed as a bendable/flexible tube (not shown in FIG. 1). The working channel 18 is provided in/inside the endoscope shaft 12 and extends from the endoscope handle 6 towards the distal tip unit 4. The working channel 18 is accessible via an access port 20. In particular, a surgical instrument may be guided through the working channel 18 into the patient's body cavity via the access port 20. The user/physician is thus able to perform medical operations such as examinations within the patient's body cavity with the surgical instrument.

The distal tip unit 4 may be tilted/bent/moved by bending the bending section 14 of the endoscope shaft 12. The endoscope 2 shown in FIG. 1 is basically a two-plane bending endoscope. This means that the distal tip unit 4 may bend in a first bending plane (e.g. in an up-and-down direction) and in a second bending plane (e.g. in a right-and-left direction). In particular, one of the handle wheels 8, 10, e.g. the first handle wheel 8, can be operated by the user to bend the distal tip unit 4 in the first bending plane and the other one of the handle wheels 8, 10, e.g. the second handle wheel 10, can be operated by the user to bend the distal tip unit 4 in the second bending plane. The first bending plane is preferably perpendicular to the second bending plane.

The bending section 14 comprises a plurality of segments including a proximal end segment 22, a plurality of intermediate segments 24 and a distal end segment 26. Two adjacent segments among the plurality of segments, i.e. a pair of segments, are connected via corresponding flexible hinge members 28, respectively. In particular, two hinge members 28 are formed between two segments. As can best be seen in FIG. 4, hinge members 28 between adjacent pairs of segments are shifted by 90°. E.g. hinge members 28 between the distal end segment 26 and an adjacent first intermediate segment 24*a* are formed at twelve and six when considering the round/circular segments as a clock, and hinge members 28 between the first intermediate segment 24*a* and an adjacent second intermediate segment 24*b* are formed at three and nine when considering the round/circular segments as a clock, and so on. Arranging the hinge members 28 like that makes it possible to bend the bending section 14 in the first bending plane and in the second bending plane. The bending section 14 essentially has a cylindrical shape/a round/circular cross-sectional shape. Referring again to FIG. 1, the bending section 14 may be largely covered by a flexible cover 30 for preventing contamination.

The endoscope 2 may comprise two steering wires 32 for controlling the bending movement of the bending section 14. One steering wire 32 of the two steering wires 32 may be connected to the first handle wheel 8 and the other one of the two steering wires 32 may be connected to the second handle wheel 10. The steering wires 32 may extend through the endoscope shaft 12. Each of the two steering wires 32 may form a loop and may thus be fixed/locked in a distal end portion of the bending section 14, in particular in the distal end segment 26. By turning the first handle wheel 8, the first steering wire 32 can be pulled and released and the distal tip unit 4 tilts according to a direction in which the first handle wheel 8 is rotated. In other words, by operating the handle wheel 8 the user is able to tilt the distal tip unit 4 in the first bending plane by bending the bending section 14 correspondingly. By turning the second handle wheel 10, the second steering wire 32 can be pulled and released and the distal tip unit 4 tilts according to a direction in which the second handle wheel 10 is rotated. In other words, by operating the handle wheel 10 the user is able to tilt the distal tip unit 4 in the second bending plane by bending the bending section 14 correspondingly.

At the distal tip unit 4, image capturing means such as a miniature video camera and illuminating means such as light-emitting diodes or fiber optic light guides connected to a proximal source of light may be arranged/installed, such that the patient's body cavity can be illuminated and inspected.

Figure 2:
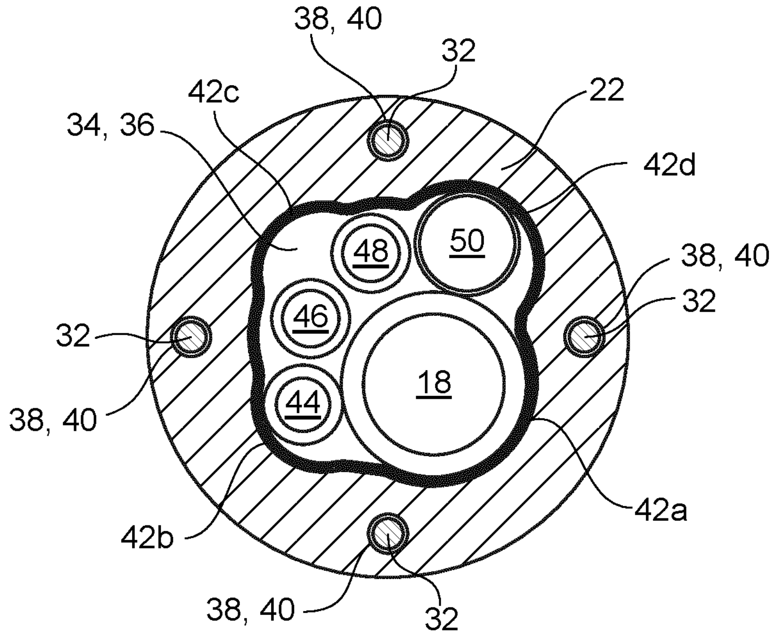
FIG. 2 is a cross-sectional view of a proximal end segment of a bending section of the endoscope according to the present disclosure.

FIG. 2 shows a cross-sectional view of the proximal end segment 22 of the bending section 14 of the endoscope 2. The proximal end segment 22 has a circular/ring-like/annular shape. A large center opening 34 is formed in the center of the proximal end segment 22. As can be seen in particular in FIG. 4 also the plurality of intermediate segments 24 and the distal end segment 26 comprise the large center opening 34. The entirety of center openings 34 forms a single inner lumen 36 as a central passage extending axially along the endoscope shaft 12.

Further, round/circular steering wire openings 38 are formed around the center opening 34 in the proximal end segment 22. The steering wire openings 38 are distributed uniformly/are angularly equally spaced (by an angle of 90°) over the circumference of the proximal end segment 22. Also the plurality of intermediate segments 24 and the distal end segment 26 comprises such round steering wire openings 38, so that the entirety of steering wire openings 38 forms four steering wire lumens 40 for accommodating the steering wire(s) 32.

As can be seen in FIG. 2, a cross-sectional shape of the single inner lumen 36/a shape of the center opening 34 is formed as a four-leaf clover such that the center opening 34 extends radially outwardly into circumferential regions/areas between adjacent steering wire lumens 40. In other words, the inner lumen 36 comprises four cut-outs/recesses 42*a*, 42*b*, 42*c*, 42*d* extending into the material of the bending section 14 between adjacent steering wire lumens 40.

Inside the inner lumen 36, several tubes are arranged, wherein, as mentioned above, one of these tubes represents the working channel 18 for guiding surgical instruments. In addition, a waterjet tube 44, a rinsing tube 46 and an insufflation tube 48 are arranged within the inner lumen 36 for flushing, rinsing and insufflating the distal tip unit 4. Furthermore, a fifth wire tube/sleeve 50 for guiding electrical wires from the endoscope handle 6 to the distal tip unit 4 is arranged within the inner lumen 36. The electrical wires can provide electrical power to a camera system and illuminating means disposed in the distal tip unit 4. The tubes comprising the working channel 18, the waterjet tube 44, the rinsing tube 46, the insufflation tube 48 and the wire tube/sleeve 50 are arranged in the inner lumen 36, such that they are essentially accommodated/supported by the corresponding cut-outs/recesses 42*a*, 42*b*, 42*c*, 42*d*. In other words, the cross-sectional shape of the inner lumen 36 is adapted to accommodate the plurality of tubes 18, 44, 46, 48 and 50. In particular, one specific cut-out 42*a* for accommodating the working channel 18 is formed between the steering wire lumens 40 at three and six when the proximal end segment 22 is seen as a clock.

Figure 3:
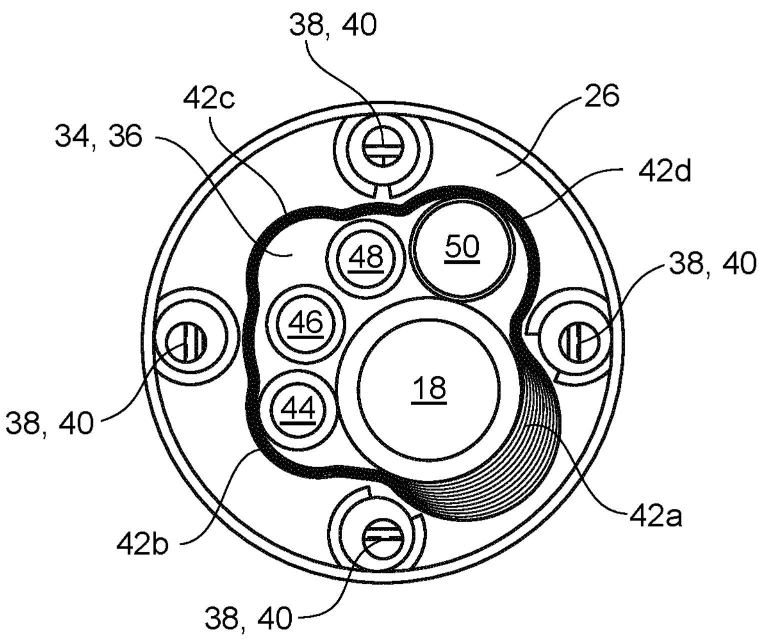
FIG. 3 is a plan view onto a distal end segment of the bending section of the endoscope according to the present disclosure.
Figure 4:
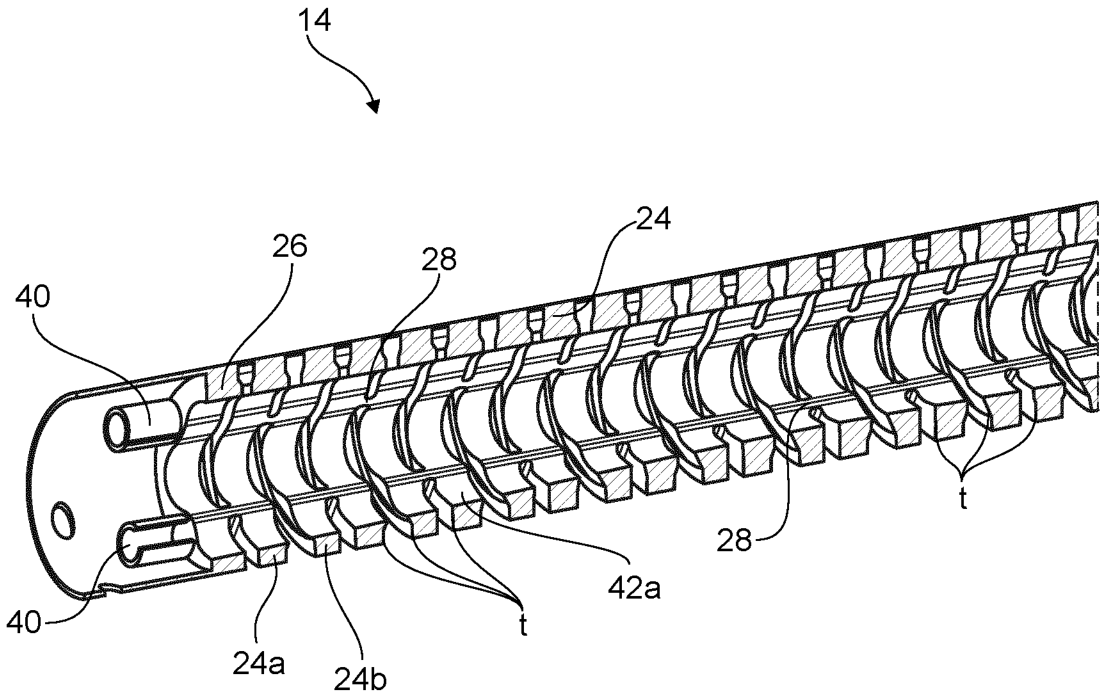
FIG. 4 is a longitudinal sectional view of the bending section of the endoscope according to the present disclosure.

As can be seen both in FIG. 3, which is a plan view onto a distal end segment 26 of the bending section 14, and in FIG. 4, which is a longitudinal sectional view of the bending section 14, a depth of this specific cut-out 42*a* for accommodating the working channel 18 gradually/continuously increases in size along the longitudinal direction of the bending section 14, i.e. the cut-out 42*a* for accommodating the working channel 18 cuts deeper into a material of the bending section 14 as it proceeds from the proximal end segment 22 to the distal end segment 26.

In other words, the inner lumen 36 has the cut-out 42*a* with the given depth into the material of the individual segments (the proximal end segment 22, the plurality of intermediate segments 24 and the distal end segment) between two steering wire lumens 40, wherein the cut-out 42*a* starts at the proximal end segment 22 of the bending section 14, and the depth of the cut-out 42*a* into the material increases towards the distal end segment 26 of the bending section 14.

As can be in particular seen in FIG. 4, the depth of the cut-out 42*a* into the material of the bending section 14 is greater in the distal end segment 26 than in an adjacent first intermediate segment 24*a*, and the depth of the cut-out 42*a* into the material of the bending section 14 is greater in the first intermediate segment 24*a* than in an adjacent second intermediate segment 24*b*, and so on.

In other words, the individual segments (the proximal end segment 22, the plurality of intermediate segments 24 and the distal end segment 26) of the bending section 14 are basically/essentially annular/ring-shaped and a thickness t in a radial direction of the ring-shaped/annular individual segments 22, 24, 26 (gradually) decreases from the proximal end segment 22 towards the distal end segment 26 of the bending section 14 in the circumferential area where the cut-out 42*a* for the working channel 18 is provided.

With the depth of the cut-out 42*a* for accommodating the working channel 18 gradually increasing in size, the working channel 18 is moved gradually from a first position near the centerline of the endoscope shaft 12 at the proximal end segment 22 to a second position closer to an outer circumference of the bending section 14 at the distal end segment 26, thereby creating space for the camera system and the illuminating means at the distal tip unit 4 without causing an abrupt deflection of the working channel 6. Thus, the risk of kinking of the working channel 18 and friction forces acting on surgical instruments being inserted into the working channel 18 can be reduced.

LIST OF REFERENCE SIGNS

2 endoscope
4 distal tip unit
6 endoscope handle
8 first handle wheel
10 second handle wheel
12 endoscope shaft
14 bending section
16 connector unit
18 working channel
20 access port
22 proximal end segment
24 intermediate segment
26 distal end segment
28 hinge members
30 flexible cover
32 steering wire
34 center opening
36 inner lumen
38 steering wire opening
40 steering wire lumen
42 cut-out/recess
44 waterjet tube
46 rinsing tube
48 insufflation tube
50 wire tube/sleeve

The invention claimed is:

1. An endoscope comprising:

a handle comprising a first handle wheel and a second handle wheel;

a distal tip unit;

a shaft connecting the distal tip unit to the handle and comprising a bending section and a central axis extending longitudinally, the first handle wheel being configured to bend the bending section along a first bending plane, and the second handle wheel being configured to bend the bending section along a second bending plane, the bending section comprising segments, an outer periphery, an inner lumen, and steering wire lumens comprising closed-periphery holes, the segments including a proximal end segment, a distal end segment and intermediate segments between the proximal end segment and the distal end segment, the segments being interconnected by hinge members, the inner lumen comprising an alternating pattern of recessed portions and lobes, the recessed portions being angularly aligned with the steering wire lumens, the lobes extending radially outwardly more than the recessed portions, and the lobes comprising a working channel tube lobe and other lobes; and a working channel tube defining at least a part of a working channel, the working channel tube extending from the handle through the shaft and being positioned in the working channel tube lobe, wherein a depth of the working channel tube lobe measured from the central axis of the bending section to a radially outwardmost point on a periphery of the working channel tube lobe gradually increases along the bending section so that the working channel tube is positioned closer to the outer periphery in the distal end segment than in the proximal end segment, and wherein a depth of each of the other lobes measured from the central axis of the bending section to a radially outwardmost point on a periphery of each of the other lobes is constant along the bending section.

2. The endoscope of claim 1, wherein the working channel tube is arranged closer to the central axis of the bending section in the proximal end segment than in the distal end segment.

3. The endoscope of claim 2, wherein the working channel tube gradually transitions from a position closer to the central axis of the bending section in the proximal end segment to a position further away from the central axis of the bending section in the distal end segment.

4. The endoscope of claim 3, wherein the bending section has a length, and wherein the working channel tube gradually transitions, along the entire length, from the position closer to the central axis of the bending section in the proximal end segment to the position further away from the central axis of the bending section in the distal end segment.

5. The endoscope of claim 1, wherein the steering wire lumens comprise a first, a second, a third, and a fourth steering wire lumen, and wherein the working channel tube lobe extends between the first and the second steering wire lumens.

6. The endoscope of claim 1, wherein the endoscope further comprises a wire tube and additional tubes, the wire tube including electrical wires extending from the handle to the distal tip unit and being accommodated in one of the other lobes.

7. The endoscope of claim 6, wherein the additional tubes include a waterjet tube, a rinsing tube, and an insufflation tube.

8. The endoscope of claim 1, wherein the intermediate segments include a first intermediate segment located adjacent the distal end segment and a second intermediate segment located proximally and adjacent the first intermediate segment, wherein the depth of the working channel tube lobe is greater in the distal end segment than the first intermediate segment, and wherein the depth of the working channel tube lobe is greater in the first intermediate segment than in the second intermediate segment.

* * * * *